United States Patent
Leclerc et al.

(10) Patent No.: US 6,825,341 B2
(45) Date of Patent: Nov. 30, 2004

(54) PROCESS FOR PREPARING FUNCTIONALIZED POLYALKYLENEIMINES, COMPOSITIONS CONTAINING THEM AND USES THEREOF

(75) Inventors: Françoise Leclerc, Bures sur Yvette (FR); Jean Herscovici, Paris (FR); Daniel Scherman, Paris (FR)

(73) Assignee: Gencell S.A., Vitry-sur-Seine (FR)

( * ) Notice: Subject to any disclaimer, the term of this patent is extended or adjusted under 35 U.S.C. 154(b) by 74 days.

(21) Appl. No.: 09/783,981

(22) Filed: Feb. 16, 2001

(65) Prior Publication Data

US 2001/0031498 A1 Oct. 18, 2001

Related U.S. Application Data

(60) Provisional application No. 60/203,907, filed on May 12, 2000.

(30) Foreign Application Priority Data

Feb. 18, 2000 (FR) .............................. 00 02059

(51) Int. Cl.$^7$ ......................... C08B 37/00; C08G 63/91
(52) U.S. Cl. ..................... 536/55.3; 525/54.2; 435/455
(58) Field of Search ................................ 514/410, 431, 514/648, 337, 657, 649, 654; 536/55.3; 525/54.2; 435/455

(56) References Cited

U.S. PATENT DOCUMENTS 5,962,400 A   10/1999   Thomaides et al.

FOREIGN PATENT DOCUMENTS

WO   WO 9742285 A   11/1997

OTHER PUBLICATIONS

Neidigh et al. J. Chem. Soc., Perkin Trans. 1, 1998, pp. 2527–2531.*

Zanta et al. Bioconjugate Chem., 1997, vol. 8, pp. 839–844.*

Zanta, M., et al., "In Vitro Gene Delivery To Hepatocytes With Galactosylated Polyethylenimine," Bioconjugate Chem. 1997, vol. 8, pp. 839–844.

Leclercq, F., et al., "Synthesis Of Glycosylated Polyethylenimine With Reduced Toxicity And High Transfecting Efficiency," Bioorganic & Medicinal Chemistry Letters, vol. 10 (2000), pp. 1233–1235.

* cited by examiner

Primary Examiner—Janet L. Epps-Ford
(74) Attorney, Agent, or Firm—Finnegan, Henderson, Farabow, Garrett & Dunner LLP

(57) ABSTRACT

The present invention relates to a process for preparing functionalized polyalkyleneimines which are useful for formulating nucleic acids intended to be transfected into cells. This process consists in treating polyalkyleneimines with a functionalized hemiacetal in the presence of titanium (IV) isopropoxide and sodium borohydride.

16 Claims, 4 Drawing Sheets

Figure 1:
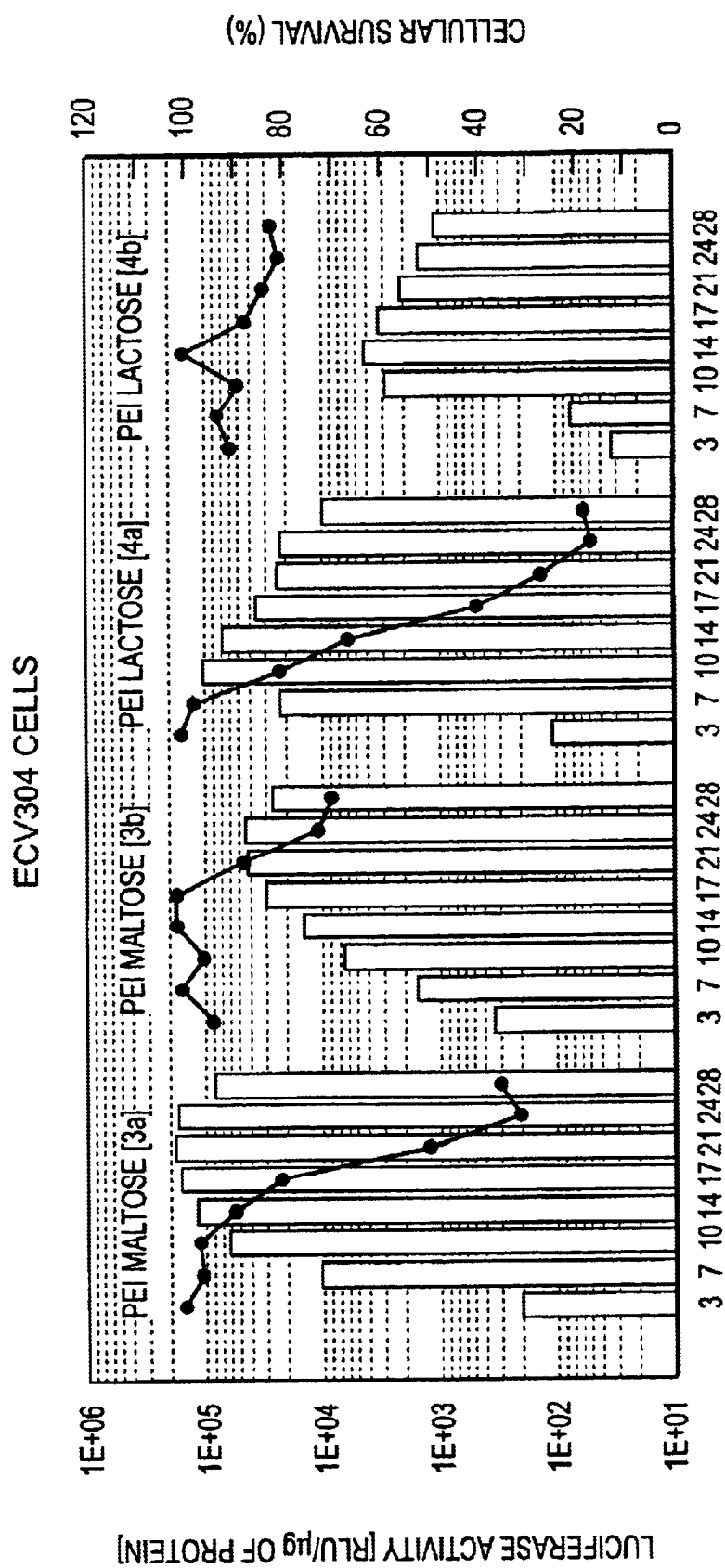

PROCESS FOR PREPARING FUNCTIONALIZED POLYALKYLENEIMINES, COMPOSITIONS CONTAINING THEM AND USES THEREOF

This application claims the benefit of French Patent Application No. 0002059, filed Feb. 18, 2000, and of U.S. Provisional Application No. 60/203,907, filed May 12, 2000, which are hereby incorporated herein by reference.

The present invention relates to a process for preparing functionalized polyalkyleneimines which are useful for formulating nucleic acids intended to be transfected into cells.

With the development of biotechnologies, the possibility of effectively transferring nucleic acids into cells has become a fundamental technique with numerous biotechnological applications. This can involve the in vitro transfer of nucleic acids into. cells, for example for the production of recombinant proteins, or in the laboratory to study the regulation of gene expression, the cloning of genes or any other manipulation involving DNA. It can also involve the in vivo transfer of nucleic acids into cells, for example to prepare vaccines, for labelling studies or for therapeutic approaches. It can also involve the transfer of genes into cells taken from an organism, for the purpose of readministering them subsequently, for example for the creation of transgenic animals.

Currently, the means most commonly used for transferring genes into cells is the use of viral vectors. However, since these are not entirely free of risks, several other methods based on the use of synthetic vectors have been proposed. These synthetic vectors have two main functions: to complex and compact the nucleic acid to be transfected, and to promote its passage across the plasma membrane and optionally across the two nuclear membranes.

Several families of synthetic vectors have thus been proposed. Among these, cationic polymers such as polyalkyleneimines are particularly advantageous. The reason for this is that they have been found to be relatively effective during the transfection of nucleic acids, in particular in vivo, and they also show relatively low toxicity. It has also been observed that the complexes they form with nucleic acids (also known as "polyplexes") diffuse relatively well out of the site of injection (J. S. Remy et al., *Advanced Drug Delivery Reviews*, 30, 1998, pp. 85–95).

Moreover, it appears at the present time to be essential to be able to provide vectors capable of targeting an appropriate nucleic acid toward an organ, a tissue, a cell type or a specific cell compartment, since it is important to be able to ensure that the nucleic acid transfected is interacting effectively with the target cells without unfavourably diffusing into the rest of the body. The intended aim is to avoid all nonspecific action of the nucleic acids on cells other than the target cells. It has thus been shown that galactosyl polyethyleneimine is an effective vector for the in vitro transfer of plasmids into cells bearing the cell receptor (lectin) corresponding to galactose (Zanta et al., *Bioconj. Chem.*, 8(2), 1997, p. 839; T. Bettinger et al., *Bioconj. Chem.*, 1999).

Hitherto, polymers such as galactosyl polyethyleneimine, for example, were obtained by the action of an oligosaccharide with the polyethyleneimine in the presence of sodium cyanoborohydride. However, this reagent has the drawback of being expensive and above all very toxic. The risk of potential presence of residual cyanide ions in the final product, which is relatively cationic, prohibits any possibility of pharmaceutical use. In addition, the search for an alternative preparation process has so far remained fruitless since polyalkyleneimines are polymers—and not small molecules—which are insoluble in many solvents, in particular apolar solvents. Thus, the use of an alternative process using sodium triacetoxyborohydride was not possible. The use of sodium borohydride in aqueous sulfuric acid and a pyridine/borane mixture was also found to be incompatible with cationic polymers. It thus appeared necessary to develop an alternative process which is compatible with cationic polymers such as polyalkyleneimines, and which involves only pharmaceutically acceptable reagents.

It has thus been found that it is possible to prepare functionalized polyalkyleneimines by treating a polyalkyleneimine with a functionalized hemiacetal in the presence of titanium (IV) isopropoxide and sodium borohydride.

Such a process has the advantage of being able to be carried out in a solvent which is compatible with polyalkyleneimines, for example such as alcohols, and only involves reagents that are both less expensive and relatively nontoxic.

Various articles from Bhattacharyya et al. (*J. Org. Chem.*, 1995, 60, pp. 4928–4929; *Synlett*, 1995, pp. 1079–1080; *J. Chem. Soc.*, Perkin Trans. 1, 1998, pp. 2527–2531) have disclosed the process below for preparing amines from ketones or aldehydes:

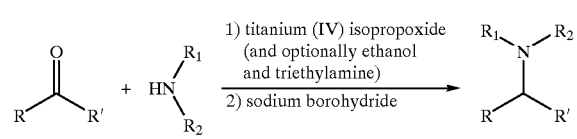

in which R and R' represent, independently of each other, a hydrogen atom, an alkyl group or an aryl group, or together form a 5-, 6- or 7-membered cycloalkyl group optionally containing a hetero atom, and $R_1$ and $R_2$ represent, independently of each other, a hydrogen atom or an alkyl group optionally substituted with a hydroxyl or an ester, or alternatively $R_1$ and $R_2$ together form a 5- or 6-membered cycloalkyl group optionally containing a hetero atom. However, such a process was described only in the context of the preparation of small molecules, i.e. in particular nonpolymeric molecules, containing only one amine function, from the corresponding ketone or aldehyde.

According to the present invention, the starting polyalkyleneimine has the general formula:

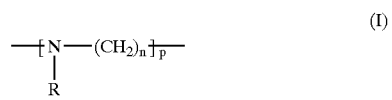

(I)

in which R represents a hydrogen atom or a group of general formula:

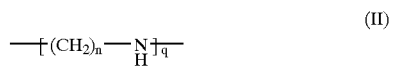

(II)

n is an integer between 2 and 10 inclusive, and p and q are integers, it being understood that the sum p+q is such that the average molecular weight of the polymer is between 100 Da and $10^7$ Da inclusive.

It is understood that, in the general formula (I), the value of n and the group R can vary between the various units —NR—$(CH_2)_n$— and —$(CH_2)_n$—NH—. Thus, the general formula I includes both linear polymers and branched polymers, as well as homopolymers and heteropolymers.

n is preferably between 2 and 5. Preferred polymers are, for example, polyethyleneimine (PEI) or polypropyleneimine (PPI). In addition, the polymers which are preferred for carrying out the present invention and which have been shown to be most particularly effective in transfection are those whose average molecular weight is between $10^3$ and $5×10^6$. By way of example, mention may be made of the polyethyleneimine of average molecular weight 50,000 Da (PEI 50K), 25,000 Da (PEI 25K) or 22,000 Da (PEI 22K) or alternatively polypropyleneimine 800,000 Da (PPI 800K).

The polyalkyleneimines used in the present invention can be obtained according to various methods known to those skilled in the art. For example, they can be synthesized chemically from the corresponding monomer(s), under anionic polymerization conditions (for example polymerization of ethyleneimine), or by reduction of polyamides obtained by polycondensation of diacids or diamines, or alternatively by reduction of imines obtained by polycondensation of dialdehydes with diamines. In addition, many polyalkyleneimines are commercially available, for example such as PEI 25K, PEI 22K or PPI 800K.

For the purposes of the invention, the expression "functionalized polyalkyleneimine" means cationic polymers of polyalkylimine type onto which targeting elements are covalently bonded. These targeting elements direct the transfer of the nucleic acid toward certain desired cell types, certain desired tissues or certain desired cell compartments. The covalent bonding between the targeting element and the polyalkyleneimine is obtained by reaction with a functionalized hemiacetal, i.e. a hemiacetal in which one of the substituents is said targeting element, under the reaction conditions mentioned previously.

More specifically, for the purposes of the present-invention, the expression "functionalized hemiacetal" means any molecule having the general formula:

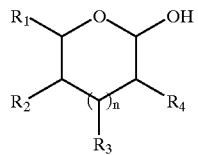

in which n is equal to 0 or 1, and $R_1$, $R_2$, $R_3$ and $R_4$ are identical or different and represent, independently of each other, a hydrogen atom, a group which is compatible with the reaction carried out or a targeting element, it being understood that one and only one of the substituents $R_1$, $R_2$, $R_3$ and $R_4$ is a targeting element.

As examples of compatible groups, mention may be made of hydroxyls, alkyls containing 1 to 4 carbon atoms (1 to 4 C) or hydroxyalkyls (1 to 4 C).

The targeting element can be either grafted directly onto the hemiacetal, or is grafted via a molecule of difunctional bonding (also known as a "linker"). The linker allows said targeting element to be grafted onto the hemiacetal, which grafting might not otherwise be possible from a chemical point of view, and/or allows said targeting element to be distanced from the hemiacetal. The expression "molecule of difunctional bonding" means any molecule comprising at least one function which can bond covalently to the targeting element and at least one function which can bond covalently to the hemiacetal.

For the purposes of the invention, the term "targeting element" means any molecule which can direct the transfer of the nucleic acid. This targeting element can be an extracellular targeting element for directing the transfer of DNA to certain desired cell types or certain desired tissues (tumor cells, liver cells, hematopoietic cells, etc.). It can also be an intracellular targeting element for directing the transfer of the nucleic acid toward certain preferred cell compartments (for example mitochondria or the nucleus).

Among the targeting elements which can be used in the context of the invention, mention may be made of sugars, peptides, proteins, oligonucleotides, lipids, neuromediators, hormones and vitamins, or derivatives thereof. Preferentially, they are, for example, sugars, peptides or proteins such as antibodies or antibody fragments, cell receptor ligands or fragments thereof, and receptors or receptor fragments. In particular, they may be growth factor receptor ligands, cytokine receptor ligands, cellular lectin receptor ligands or ligands of RGD sequence with an affinity for the receptors of adhesion proteins such as the integrins. Mention may also be made of transferin receptors, HDLs and LDLs, or the folate transporter. The targeting element can also be a sugar for targeting lectins such as the receptors for asialoglycoproteins or for sialyls such as Sialyl Lewis X, or alternatively an antibody fragment Fab, or a single-chain antibody (ScFv). By way of example, said sugar can be chosen from mono-, di- or trisaccharides. It can be, for example, galactose, mannose, fucose, rhamnose, lactose or maltose.

The reaction is generally carried out in an alcoholic solvent, for example methanol or ethanol, at a temperature of between 100° C. and 30° C. The process is preferably performed in ethanol at room temperature, i.e. at a temperature of between 18° C. and 25° C.

In addition, between 25 mol and 100 mol of titanium(IV) isopropoxide are generally used per mole of polymer introduced, and more preferably between 40 mol and 60 mol of titanium(IV) isopropoxide per mole of polymer.

An amount of sodium borohydride equal to 50% to 80% (molar) of the amount of titanium(IV) isopropoxide used is also introduced into the reaction mixture.

The amount of functionalized hemiacetal used to carry out the process according to the invention depends on the degree of grafting which it is desired to obtain. Between 6 mol and 100 mol of functionalized hemiacetal are advantageously used per mole of polymer.

According to the amount of functionalized hemiacetal used, polyalkyleneimines which are functionalized to degrees which can range between 1% and 20%, and preferably between 4% and 20%, are obtained. When a sugar is used as targeting element, the percentage of sugars grafted onto the polyalkyleneimine can be determined specifically using the resorcinol method. This method consists in treating the predialyzed functionalized polyalkyleneimine with resorcinol and sulfuric acid, followed by heating at 90° C. for 20 minutes. After cooling, the absorbance at 495 nm is measured and compared with a reference sample (standard solution). The dialysis removes the ungrafted targeting elements, and the measurement made in comparison with a reference sample determines the amount of targeting elements grafted. This method moreover constitutes one of the most reliable means for characterizing the product obtained since, as it involves polymers, it is not possible to characterize them by NMR (nuclear magnetic resonance) or by measuring their mass, as is conventionally done for small molecules.

The process according to the present invention is particularly advantageous since it constitutes an alternative process, which is both inexpensive and relatively nontoxic, for preparing nucleic acid transfer vectors which are capable of targeting certain specific tissues, certain specific cell types or certain specific cell compartments. In addition, it has been noted that the polyalkyleneimines functionalized with sugars are less toxic with respect to cells than nonfunctionalized polyalkyleneimines.

Functionalized polyalkyleneimines are useful for transfecting nucleic acids into cells. With this aim, the functionalized polyalkyleneimines are mixed with one or more nucleic acids so as to form complexes also known as "polyplexes" (in this case, the process may be referred to as "polyfection" rather than transfection). In order to obtain optimal transfection efficacy, the proportions of functionalized polyalkyleneimine and of nucleic acid are preferably chosen such that the polyplex formed is neutral or slightly positive overall. In general, said proportions are chosen so as to form positive polyplexes which do not precipitate, without, however, excessively increasing the cationic nature of the polyplexes formed, since this also increases the toxicity. Said proportions should thus be determined on a case by case basis. However, said proportions are generally chosen so that the molar ratio between the amines in the functionalized polyalkyleneimine and the phosphates in the nucleic acid is between 0.1 and 50, preferably between 0.5 and 20. Needless to say, this ratio can be readily adapted and optimized by a person skilled in the art depending on the functionalized polyalkyleneimine used, the nucleic acid, the target cell, the method of administration or according to the applications envisaged (in particular the type of cells to be transfected).

In the polyplexes as described above, the nucleic acid can be either a deoxyribonucleic acid or a ribonucleic acid. It can involve natural or artificial sequences, and in particular genomic DNA (gDNA), complementary DNA (cDNA), messenger RNA (mRNA), transfer RNA (tRNA), ribosomal RNA (rRNA), hybrid sequences or synthetic or semisynthetic sequences, of modified or unmodified oligonucleotides. These nucleic acids can be, for example, of human, animal, plant, bacterial or viral origin. They can be obtained by any technique known to those skilled in the art, and in particular by screening libraries, by chemical synthesis or by mixed methods including chemical or enzymatic modification of sequences obtained by screening libraries. They can be chemically modified.

As more particularly regards deoxyribonucleic acids, they can be single- or double-stranded as well as short oligonucleotides or longer sequences. In particular, the nucleic acids advantageously consist, for example, of plasmids, vectors, episomes or expression cassettes. These deoxyribonucleic acids can in particular carry a functional or non-functional origin of replication into the target cell, one or more marker genes, sequences for regulating transcription or replication, genes of therapeutic interest, modified or unmodified antisense sequences, or regions for binding to other cell components.

The nucleic acid preferably comprises one or more genes of therapeutic interest under the control of regulatory sequences, for example one or more promoters and a transcription terminator, which are active in the target cells.

For the purposes of the invention, the expression "gene of therapeutic interest" in particular means any gene encoding a protein product which has a therapeutic effect. The protein product thus encoded can be in particular a protein or a peptide. This protein product may be exogenous, homologous or endogenous with respect to the target cell, i.e. a product which is normally expressed in the target cell when this cell shows no other pathology. In this case, the expression of a protein makes it possible, for example, to overcome an insufficient expression in the cell or the expression of a protein which is inactive or only weakly active on account of a modification, or alternatively to overexpress said protein. The gene of therapeutic interest can also encode a mutant of a cell protein, having, for example, increased stability or a modified activity. The protein product can also be heterologous with respect to the target cell. In this case, a protein expressed can, for example, complement or provide an activity that is deficient in the cell, enabling the cell to combat a pathology, or to stimulate an immune response.

Among the products that are therapeutic for the purposes of the present invention, mention may be made, for example, of enzymes, blood derivatives, hormones, lymphokines (for example interleukins, interferons or TNF: FR 92/03120), growth factors, neurotransmitters or precursors thereof or synthesis enzymes, trophic factors (for example BDNF, CNTF, NGF, IGF, GMF, aFGF, bFGF, VEGF, NT3, NT5 or HARP/pleiotrophin), apolipoproteins (for example ApoAI, ApoAIV or ApoE: FR 93/05125), dystrophin or a minidystrophin (FR 91/11947), the CFTR protein associated with mucoviscidosis, tumor-suppressing genes (for examples p53, Rb, Rap1A, DCC or k-rev: FR 93/04745), genes encoding factors involved in clotting (for example Factors VII, VIII and IX), genes involved in DNA repair, suicide genes (thymidine kinase, cytosine deaminase), the genes for hemoglobin or other protein transporters, and metabolic or catabolic enzymes.

The nucleic acid of therapeutic interest can also be a gene or an antisense sequence whose expression in the target cell makes it possible to control the expression of genes or the transcription of cellular mRNA. Such sequences can be transcribed, for example, into the target cell as RNA which is complementary to cellular mRNA and thus block its translation into protein, according to the technique described in patent EP 140 308. The therapeutic genes also comprise sequences encoding ribozymes, which are capable of selectively destroying target RNAs (EP 321 201).

As indicated above, the nucleic acid can also comprise one or more genes encoding an antigenic peptide, which are capable of generating an immune response in man or animals. In this specific embodiment, the invention allows the production either of vaccines or of immunotherapeutic treatments applied to man or animals, in particular against microorganisms, viruses or cancers. They can be, in particular, antigenic peptides specific for the Epstein-Barr virus, the HIV virus, the hepatitis B virus (EP 185 573), the pseudorabies virus, the "syncitia forming virus", other viruses or antigenic peptides specific for tumors (EP 259 212).

The nucleic acid also preferably comprises sequences allowing the expression of the gene of therapeutic interest and/or the gene encoding the antigenic peptide in the desired cell or organ. These may be sequences which are naturally responsible for the expression of the gene under consideration when these sequences are capable of functioning in the infected cell. They may also be sequences of different origin (responsible for the expression of other proteins, or even synthetic). They may in particular be promoter sequences of eukaryotic or viral genes. For example, they may be promoter sequences originating from the genome of the cell which it is desired to infect. Similarly, they may be promoter sequences originating from the genome of a virus. In this respect, mention may be made, for example, of the promoters of the E1A, MLP, CMV or RSV genes. In addition, these expression sequences can be modified, for example by adding activating or regulatory sequences. The sequence can also be an inducible or repressible promoter.

The polyplexes thus formed can be formulated for the purpose of topical, cutaneous, oral, rectal, vaginal, parenteral, intranasal, intravenous, intramuscular, subcutaneous, intraocular, transdermal, intratracheal or intraperitoneal administration, for example. The polyplexes formed preferably contain a vehicle which is pharmaceutically acceptable for an injectable formulation, in particular for direct injection into the desired organ, or for topical administration (onto skin and/or mucous membrane). They can be, in particular, sterile, isotonic solutions or dry compositions, in particular lyophilized compositions, which on addition of sterilized water or physiological saline, depending on the case, allow injectable solutions to be made up. The doses of nucleic acids used for the injection and the number of administrations can be adapted as a function of various parameters, and in particular as a function of the method of administration used, the pathology concerned, the gene to be expressed or the desired duration of the treatment. As more particularly regards the method of administration, this can be either a direct injection into the tissues, for example into tumors, or into the circulatory systems, or a treatment of cells in culture followed by their in vivo reimplantation, by injection or grafting. The tissues concerned in the context of the present invention are, for example, the muscles, the skin, the brain, the lungs, the liver, the spleen, bone marrow, the thymus, the heart, the lymph, the blood, the bones, the cartilages, the pancreas, the kidneys, the bladder, the stomach, the intestines, the testicles, the ovaries, the rectum, the nervous system, the eyes, the glands or connective tissues.

The compositions comprising the polyplexes as described above can be used for transferring nucleic acids into cells. More specifically, said compositions can be used to prepare a medicinal product intended for treating diseases, in particular diseases resulting from a deficiency of a protein product or nucleic acid product.

One method for transferring the nucleic acids into cells consists in carrying out the following steps:

(1) forming a composition comprising the polyplexes as described above, and
(2) placing the cells in contact with the composition formed in (1).

Besides the preceding arrangements, the present invention also comprises other characteristics and advantages which will emerge from the examples and figures which follow, and which should be considered as illustrating the invention without limiting its scope.

FIGURES

FIG. 1: histogram representing the luciferase activity in RLU/µg of proteins (RLU: "Relative Light Unit") in ECV304 cells for various glycosyl polyalkyleneimine/DNA formulations at charge ratios (+/−) ranging from 3 to 28.

The curve as a continuous black line represents the percentage of cellular survival according to the charge ratio (+/−) between the glycosyl polyalkyleneimine and the DNA for each formulation [3a], [3b], [4a] and [4b] used.

Figure 2:
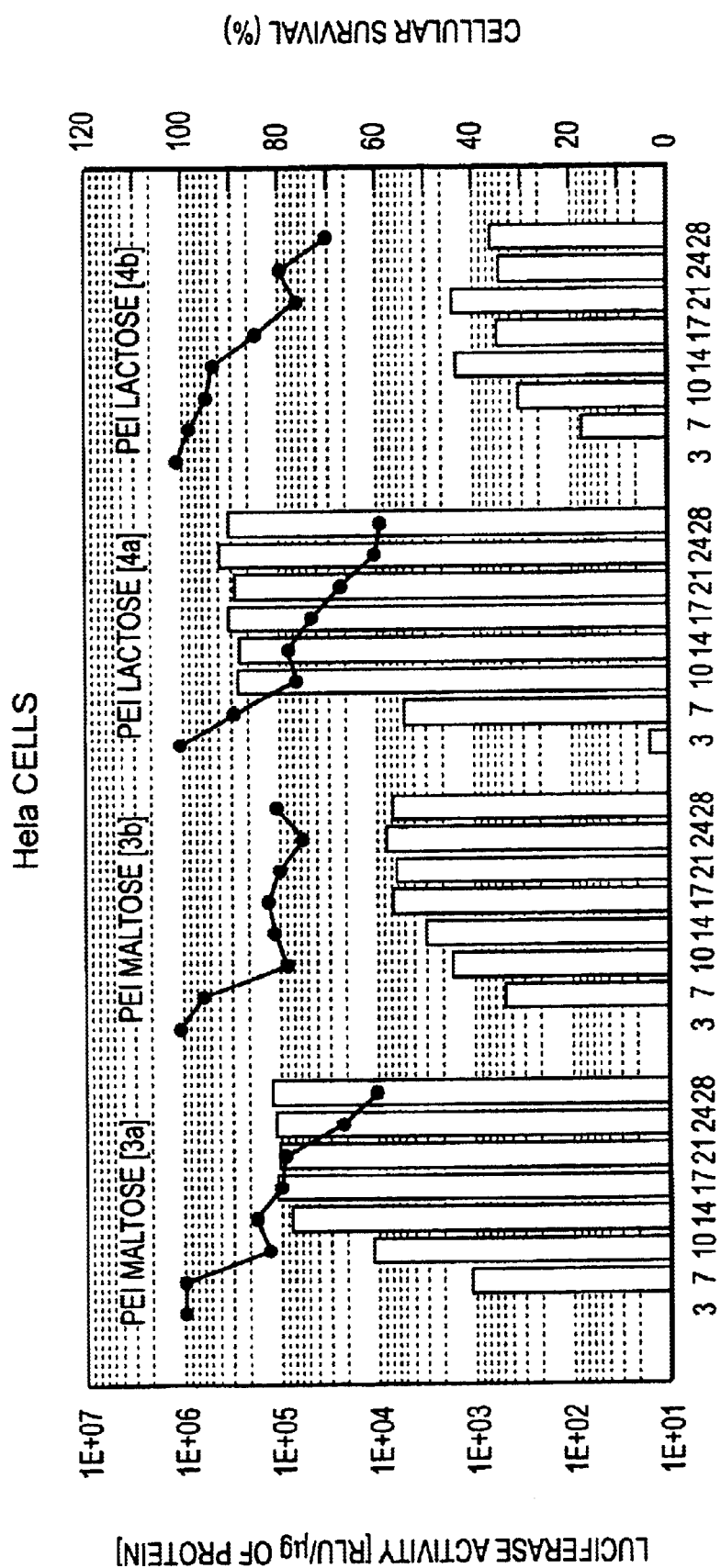

FIG. 2: histogram representing the luciferase activity in RLU/µg of proteins (RLU: "Relative Light Unit") in HeLa cells for various glycosyl polyalkyleneimine/DNA formulations at charge ratios (+/−) ranging from 3 to 28.

The curve as a continuous black line represents the percentage of cellular survival according to the charge ratio (+/−) between the glycosyl polyalkyleneimine and the DNA for each formulation [3a], [3b], [4a] and [4b] used.

Figure 3:
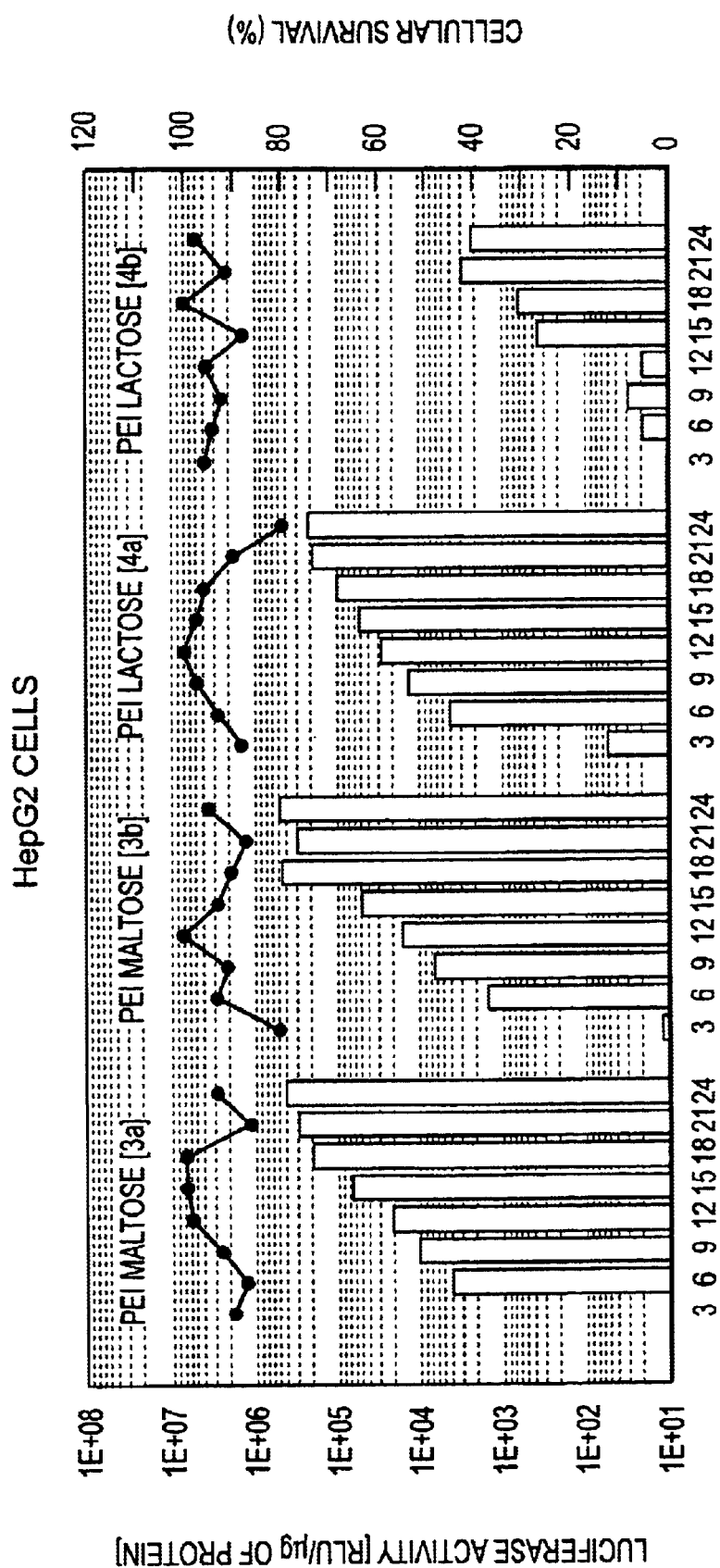

FIG. 3: histogram representing the luciferase activity in RLU/µg of proteins (RLU: "Relative Light Unit") in HepG2 cells for various glycosyl polyalkyleneimine/DNA formulations at charge ratios (+/−) ranging from 3 to 28.

The curve as a continuous black line represents the percentage of cellular survival according to the charge ratio (+/−) between the glycosyl polyalkyleneimine and the DNA for each formulation [3a], [3b], [4a] and [4b] used.

Figure 4:
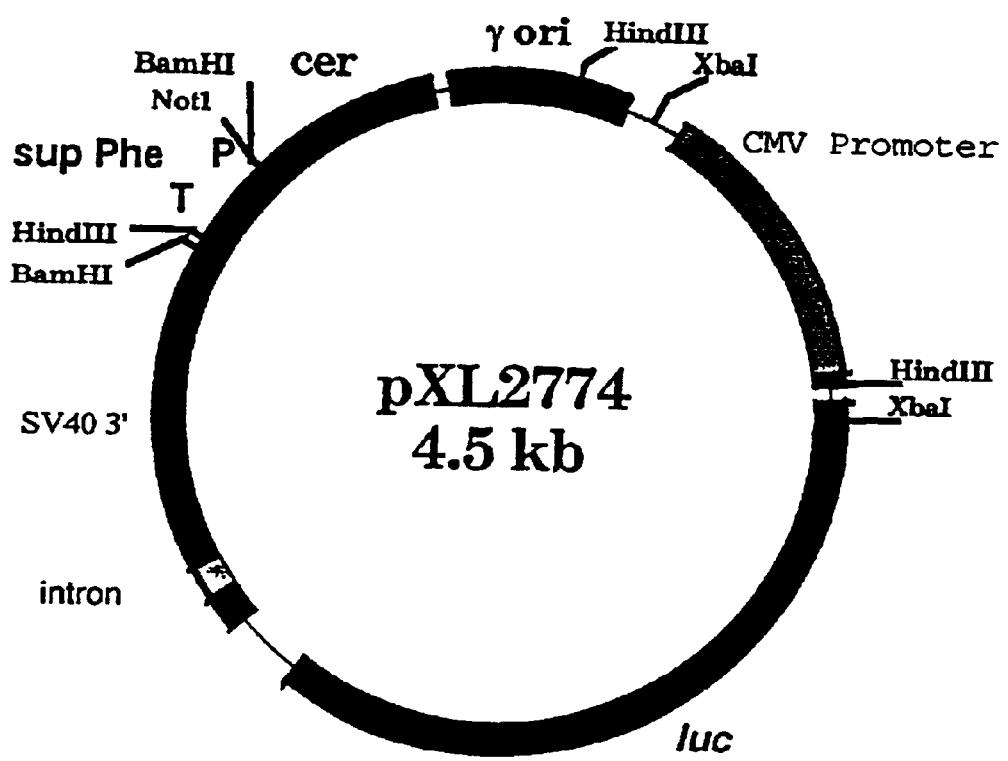

FIG. 4: schematic representation of the plasmid pXL2774 used in the experiments of DNA transfer into the cells.

EXAMPLES

Example 1

Preparation of 4% PEI-Maltose [3a]

The reaction carried out can be written schematically in the following way:

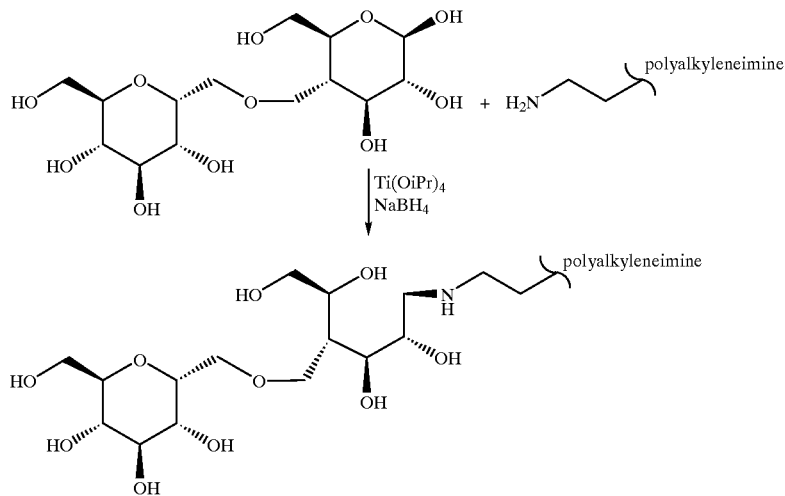

0.02 mmol of PEI 25 KDa (500 mg, from Aldrich) is dissolved in 20 ml of anhydrous ethanol. 0.7 mmol of maltose (252 mg) is then added and the solution thus obtained is mixed under a nitrogen atmosphere for 15 minutes. 1 mmol of titanium IV isopropoxide (0.3 ml) is added slowly to the reaction mixture and stirring is continued overnight. 0.75 mmol of sodium borohydride (28.5 mg) is then added and stirring is continued for 8 hours. The reaction mixture is then filtered and concentrated to 10 ml. The resulting solution is finally dialyzed for 12 hours (exclusion membrane of size 12000). The yield is 80%.

The percentage of grafted maltose residues is determined by the resorcinol method described previously: 23 maltose residues are grafted onto the PEI 25 KDa, corresponding to a degree of grafting of the amino groups of 4%.

Example 2

Preparation of 12% PEI-Maltose [3b]

0.02 mmol of PEI 25 KDa (500 mg, from Aldrich) is dissolved in 20 ml of anhydrous ethanol. 2 mmol of maltose (720 mg) are then added and the solution thus obtained is mixed under a nitrogen atmosphere for 15 minutes. 2.7 mmol of titanium IV isopropoxide (0.8 ml) are added slowly to the reaction mixture and stirring is continued overnight.

2 mmol of sodium borohydride (76 mg) are then added and stirring is continued for 8 hours. The reaction mixture is then filtered and concentrated to 10 ml. The resulting solution is finally dialysed for 12 hours (exclusion membrane of size 12000). The yield is 80%.

The percentage of grafted maltose residues is determined by the resorcinol method described previously: 70 maltose residues are grafted onto the PEI 25 KDa, corresponding to a degree of grafting of the amino groups of 12%.

Example 3

Preparation of 6% PEI-Lactose [4a]

The reaction carried out can be written schematically in the following way:

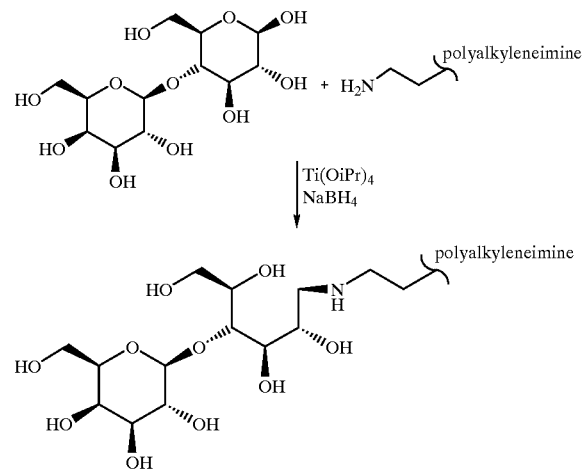

0.02 mmol of PEI 25 KDa (500 mg, from Aldrich) is dissolved in 20 ml of anhydrous ethanol. 1 mmol of lactose (360 mg) is then added and the solution thus obtained is mixed under a nitrogen atmosphere for 15 minutes. 1.35 mmol of titanium IV isopropoxide (0.4 ml) are added slowly to the reaction mixture and stirring is continued overnight. 1 mmol of sodium borohydride (38 mg) is then added and stirring is continued for 8 hours. The reaction mixture is then filtered and concentrated to 10 ml. The resulting solution is finally dialysed for 12 hours (exclusion membrane of size 12000). The yield is 80%.

The percentage of grafted lactose residues is determined by the resorcinol method described previously: 35 lactose residues are grafted onto the PEI 25 KDa, corresponding to a degree of grafting of the amino groups of 6%.

Example 4

Preparation of 17% PEI-Lactose [4b]

0.02 mmol of PEI 25 KDa (500 mg, from Aldrich) is dissolved in 20 ml of anhydrous ethanol. 3 mmol of lactose (1080 mg) are then added and the solution thus obtained is mixed under a nitrogen atmosphere for 15 minutes. 4 mmol of titanium IV isopropoxide (1.2 ml) are added slowly to the reaction mixture and stirring is continued overnight. 3 mmol of sodium borohydride (114 mg) are then added and stirring is continued for 8 hours. The reaction mixture is then filtered and concentrated to 10 ml. The resulting solution is finally dialysed for 12 hours (exclusion membrane of size 12000). The yield is 80%.

The percentage of grafted lactose residues is determined by the resorcinol method described previously: 99 lactose residues are grafted onto the PEI 25 KDa, corresponding to a degree of grafting of the amino groups of 17%.

Example of Use

In vitro Transfection of Plasmid DNA Complexed with 4% and 12% PEI-Maltose or with 6% and 17% PEI-Lactose in Various Cell Types.

This example illustrates the capacity of the functionalized polyalkyleneimines synthesized above to transfect DNA into cells.

The DNA used is the plasmid pXL2774 dissolved in a mixture of 150 mM sodium chloride to a concentration of 80 µg/ml. This plasmid contains the luc gene encoding luciferase under the control of cytomegalovirus CMV promoter. It is 4500 bp in size. The scheme of this plasmid is represented in FIG. 4. The plasmid pXL2774 was purified according to the methods described in patent application WO 97/35002.

The polyplexes are prepared by mixing a solution of plasmid pXL2774 volume for volume with a solution of functionalized PEI diluted in water to variable concentrations depending the desired charge ratio.

24-Well microplates are inoculated with 60,000 HeLa cells (ATCC) per well, and transfected 24 hours later. 50 µl of the solution of polyplexes are added dropwise into each well. In the absence of serum, the medium was supplemented beforehand with FCS (fetal calf serum) 2 hours before the transfection. The cells are then incubated at 37° C. for 4 hours. The medium containing the complexes is then removed and replaced with a mixture of DMEM and 10% fetal calf serum. Next, the cells are cultured again for 24 hours. Finally, the cells are lyzed and tested using a luciferase test kit (Promega) and a Dynex MLX luminometer. In addition, the toxicity of the polyplexes was evaluated by measuring the concentrations of the cell lyzate and expressed as enzymatic activity per µg of proteins in the lyzate.

The results shown in FIGS. 1, 2 and 3 indicate the transfection efficacy with the various functionalized PEIs synthesized above for variable charge ratios with DNA and in 3 different cell lines.

It is found overall that the transfer efficacy is relatively high except when polyplexes formed from PEI with a high degree of grafting are used (efficacy with 12% PEI-maltose is lower than that with 4% PEI-maltose and efficacy with 17% PEI-lactose is lower than that with 6% PEI-lactose). The degree of grafting is thus a parameter which it is important to optimize depending on the applications envisaged.

In addition, it has been found that substitution of the amino groups with a functionalized hemiacetal significantly reduces the toxicity induced by PEI with respect to cells, in particular at a high DNA charge ratio. Specifically, the percentage of survival of the cells (FIGS. 1, 2 and 3) remains much higher than that which is obtained using nonfunctionalized PEI to transfect the DNA (result not shown).

Thus, this example show that the functionalized polyalkyleneimines obtained by the process according to the present invention, which is reliable and inexpensive, are good candidates for transfecting DNA into cells.

What is claimed is:

1. A process for making functionalized polyalkyleneimines, comprising treating a polyalkyleneimine with a functionalized hemiacetal in the presence of titanium (IV) isopropoxide and sodium borohydride.

2. The process according to claim 1, further comprising an alcoholic solvent.

3. The process according to claim 2, wherein the alcoholic solvent is methanol or ethanol.

4. The process according to claim 1, which is performed at a temperature between about 10° C. and about 30° C.

5. The process according to claim 1, wherein between about 25 mol and about 100 mol of titanium (IV) isopropoxide are used per mol of polyalkyleneimine.

6. The process according to claim 1, wherein a molar mount of sodium borohydride is used equal to between 50% and 80% of the molar amount of titanium (IV) isopropoxide.

7. The process according to claim 1, wherein between about 6 mol and about 100 mol of functionalized hemiacetal are used per mol of polyalkyleneimine.

8. The process according to claim 1, wherein the polyalkyleneimine has the general formula:

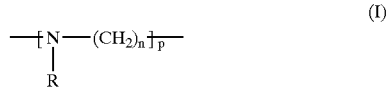

(I)

wherein R is hydrogen or a group of the general formula:

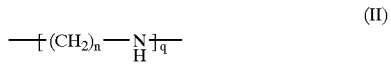

(II)

wherein n is an integer between 2 and 10 inclusive;
wherein p and q are integers; and
wherein the sum of p+q is such that an average polymer molecular weight is between about 100 Da and about $10^7$ Da.

9. The process according to claim 8, wherein the polyalkyleneimine is polyethyleneimine or polypropyleneimine.

10. The process according to claim 9, wherein the polyethyleneimine has an average molecular weight of about 50,000 Da, about 25,000 Da, or about 22,000 Da.

11. The process according to claim 9, wherein the polypropyleneimine has an average molecular weight of about 800,000 Da.

12. The process according to claim 1, wherein the functionalized hemiacetal has the general formula:

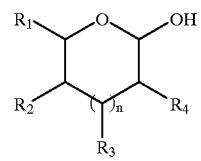

wherein n is 0 or 1;

$R_1$, $R_2$, $R_3$, and $R_4$ are independently hydrogen, a group compatible with he process according to claim 1, or a targeting element that directs the transfer of a nucleic acid toward specific cell types, specific tissues, or specific cell compartments; and only one of $R_1$, $R_2$, $R_3$, and $R_4$ is a targeting element.

13. The process according to claim 12, wherein the group which is compatible with the reaction is chosen from hydroxyls, C1–C4 alkyls, and C1–C4 hydroxyalkyls.

14. The process according to claim 12, wherein the targeting element is chosen from sugars, peptides, proteins, oligonucleotides, lipids, neuromediators, hormones, vitamins, and derivatives thereof.

15. The process according to claim 12, wherein the targeting element is chosen from growth factor receptor ligands, cellular lectin receptor ligands, cytokine receptor ligands, ligands of RGD sequences with an affinity for the receptors of adhesion proteins, transferring receptors, high density lipoproteins, low density lipoproteins, the folate transporter, Sialyl Lewis X, antibody fragments, single-chain antibodies (ScFv), monoglycerides, diglycerides, and triglycerides.

16. The process according to claim 15, wherein between about 1% and about 20% of the functionalized hemiacetal is grafted onto the polyalkyleneimine.

* * * * *

UNITED STATES PATENT AND TRADEMARK OFFICE
CERTIFICATE OF CORRECTION

PATENT NO. : 6,825,341 B2
DATED : November 30, 2004
INVENTOR(S) : Leclercq et al.

It is certified that error appears in the above-identified patent and that said Letters Patent is hereby corrected as shown below:

Title page,
Item [12], "Leclerc," should read -- Leclercq, --.
Item [75], Inventors, "Leclerc," should read -- Leclercq, --.

Column 11,
Line 7, "mount" should read -- amount --.

Column 12,
Line 12, "he" should read -- the --.

Signed and Sealed this

Twenty-sixth Day of April, 2005

JON W. DUDAS
*Director of the United States Patent and Trademark Office*